Figure 1:
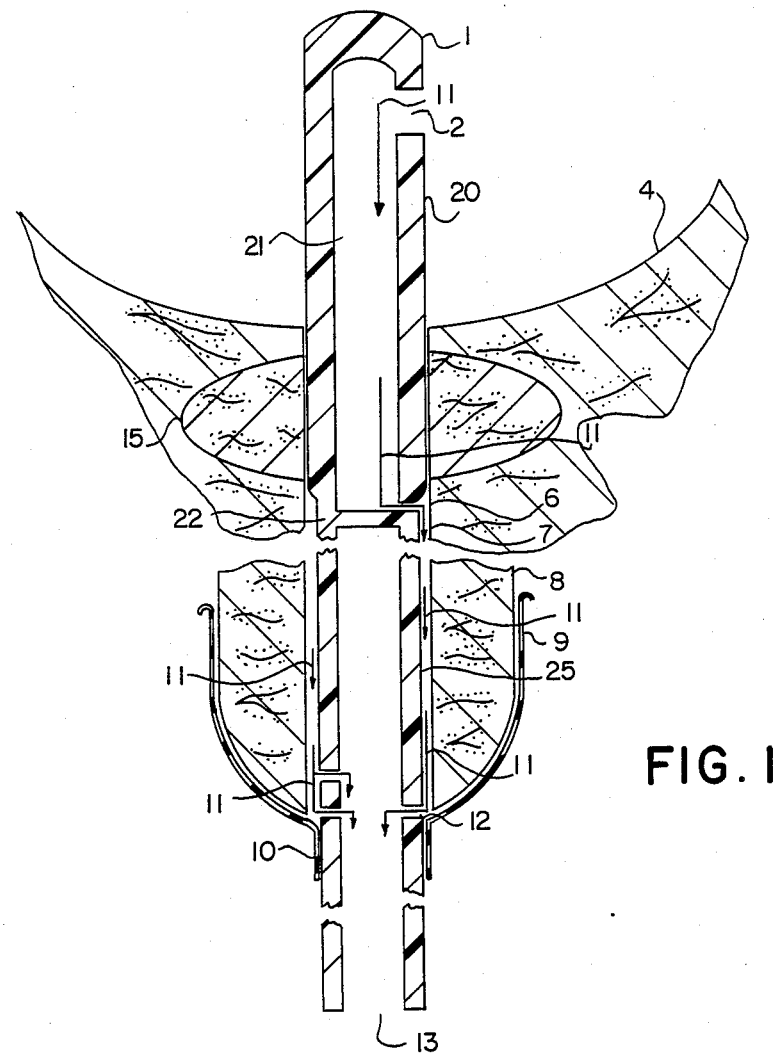

United States Patent [19]
Sachse

[11] Patent Number: 4,878,901
[45] Date of Patent: Nov. 7, 1989

[54] CONDOM CATHETER, A URETHRAL CATHETER FOR THE PREVENTION OF ASCENDING INFECTIONS

[76] Inventor: Hans-Ernst Sachse, 8500 Nuernberg 90, Lerchenstr. 55, Fed. Rep. of Germany

[21] Appl. No.: 129,448

[22] Filed: Dec. 7, 1987

[51] Int. Cl.[4] .................................................. A61M 5/32
[52] U.S. Cl. ...................................... 604/174; 604/101; 604/102
[58] Field of Search .......................... 604/101, 102, 174

[56] References Cited

U.S. PATENT DOCUMENTS

| 871,474 | 11/1907 | Buckner | 604/102 |
|---|---|---|---|
| 1,661,494 | 3/1928 | Nielsen | 604/174 |
| 2,547,758 | 4/1951 | Keeling | 604/174 |
| 2,642,874 | 6/1953 | Keeling | 604/101 |
| 2,693,191 | 11/1954 | Raiche | 604/101 |
| 2,799,273 | 7/1957 | Oddo | 604/101 |
| 3,459,175 | 8/1969 | Miller | 604/174 |
| 3,630,206 | 12/1971 | Gingold | 604/102 |
| 4,335,723 | 6/1982 | Patel | 604/101 |
| 4,579,554 | 4/1986 | Glassman | 604/102 |
| 4,660,560 | 4/1987 | Klein | 604/101 |

FOREIGN PATENT DOCUMENTS

| 1913976 | 10/1969 | Fed. Rep. of Germany | 604/174 |
|---|---|---|---|
| 3306342 | 8/1984 | Fed. Rep. of Germany . | |
| 3321877 | 12/1984 | Fed. Rep. of Germany . | |
| 3202713 | 2/1986 | Fed. Rep. of Germany . | |

Primary Examiner—C. Fred Rosenbaum
Assistant Examiner—Kathleen A. Daley
Attorney, Agent, or Firm—Keil & Weinkauf

[57] ABSTRACT

An indwelling urethral catheter arrangement for the prevention of ascending bacterial infection which is of such a design that, on the one hand the bacteria are flushed downwardly by urine permitted to flow along the inside of the urethral wall and, on the other hand, the entire urinary stream is conducted, with the aid of a condom-like sheath fittable over the tip of the penis, to the outside of the catheter arrangement; in this fashion soiling of the patient's clothing will be avoided regardless of the flushing provision.

5 Claims, 5 Drawing Sheets

CONDOM CATHETER, A URETHRAL CATHETER FOR THE PREVENTION OF ASCENDING INFECTIONS

In the male, the foremost section of the urethra as viewed from the urethral orifice is always populated with bacteria trying by way of population growth and spontaneous movement to ascent in the direction of the bladder. The urinary stream is generally opposed to this tendency and flushes the bacteria outside again. This normally existing cleansing mechanism is put out of function by the placement of an indwelling urethral catheter. A mucosal layer will form between the wall of the indwelling catheter and the wall of the urethra, in which the bacteria can grow unrestrainedly in the direction of the bladder. Depending on the prevailing type of bacteria, these organisms will reach the bladder within a few hours and infect it. The structural features of the catheter described in Pat. No. DE 3202713 C2 and additional applications P 33 21 877.3 and P 33 06 342.7 are trying to imitate this natural flushing mechanism. In order to achieve the desired flushing effect, the urine flows in the region of a middle catheter section between the outer catheter wall and the urethral wall in the direction of the urethral orifice before flowing back into the catheter lumen and subsequently outside. This way, the space between catheter wall and urethral wall is continuously flushed free from bacteria. Inasmuch as its mode of action is concerned, this catheter principle has already proven itself. It has, however, been found that with such catheter configurations it is not possible to achieve a reliable sealing effect between cather wall and urethral orifice, so that part of the urine will exit beside the urethral orifice, thus soiling the patient's clothing.

The object of the present invention is to eliminate this very unpleasant nuisance which makes the patient socially unacceptable.

At the first instance, this aim can be achieved by the features described under claim 1. Here, the urine will only return to the inner lumen of the catheter through one or several openings and then exit to the outside after having passed a long section between urethral wall and external catheter wall. At the same time, a firmly adhering or possibly self-adhesive condom-type rubber sheath fitted like a condom over the glans and the body of the penis prevents the urine from exiting into the surroundings.

A further advantageous embodiment of said condom catheter is the subject matter of claim 2. Here, the catheter tip is kept permanently in its correct position within the bladder by means of a balloon. This catheter with its very simple design features is suitable for patients who do not have erections. Owing to the fact that length problems will be encountered in the case of a penis erection when using the catheter according to claim 2, the catheter according to claim 3 is of variable length in its middle section. In said middle section the catheter shaft is configured similar to the bellows of an accordion and can, if subjected to light tension in the case of a penis erection, increase the distance between the catheter balloon positioned in the bladder and the urethral orifice.

In order to circumvent the catheter design according to claim 3 which is certainly complicated and expensive to manufacture, and in order to bother the patient with as little "catheter irritation" as possible, the catheter shaft proper according to claim 4 in the form of an "inner urethral catheter" is only located in the region of the posterior urethra, in the region of the two sphincter muscles, and the prostate. Hereby, said catheter is fixed in its correct position by means of one catheter balloon positioned in the bladder and a second one positioned in the posterior urethra.

The filling channels for the two balloons are located within narrow tubes fitted with small filling nozzles at their ends. Said commercially available filling nozzles are located easily accessible outside the urethral orifice and inside the outlet funnel of the condom-type rubber sheath or are in said region accessible from the outside and allow to fill up the balloons.

This short "inner catheter" is introduced by means of a special guiding mandrin according to claim 5. For the purpose of introducing the catheter, said "inner catheter" is placed over the guiding mandrin which is shaped to suit the inner lumen of the "inner catheter". The clamping effect is produced by a wedge being pulled into the mandrin shaft which is split in its foremost section, thus expanding the tip of the mandrin. After correct positioning and relaxing of the clamping mechanism, the mandrin can be easily removed. The inner catheter can be removed by pulling at the two filling tubes after the two balloons have been emptied.

Additional advantages and features of the invention are given in the additional sub-claims as well as in the subsequent description with relevant drawings of embodiments according to the invention. The drawings show in:

FIG. 1: A longitudinal section of the condom catheter in its simplest configuration.

Figure 2:
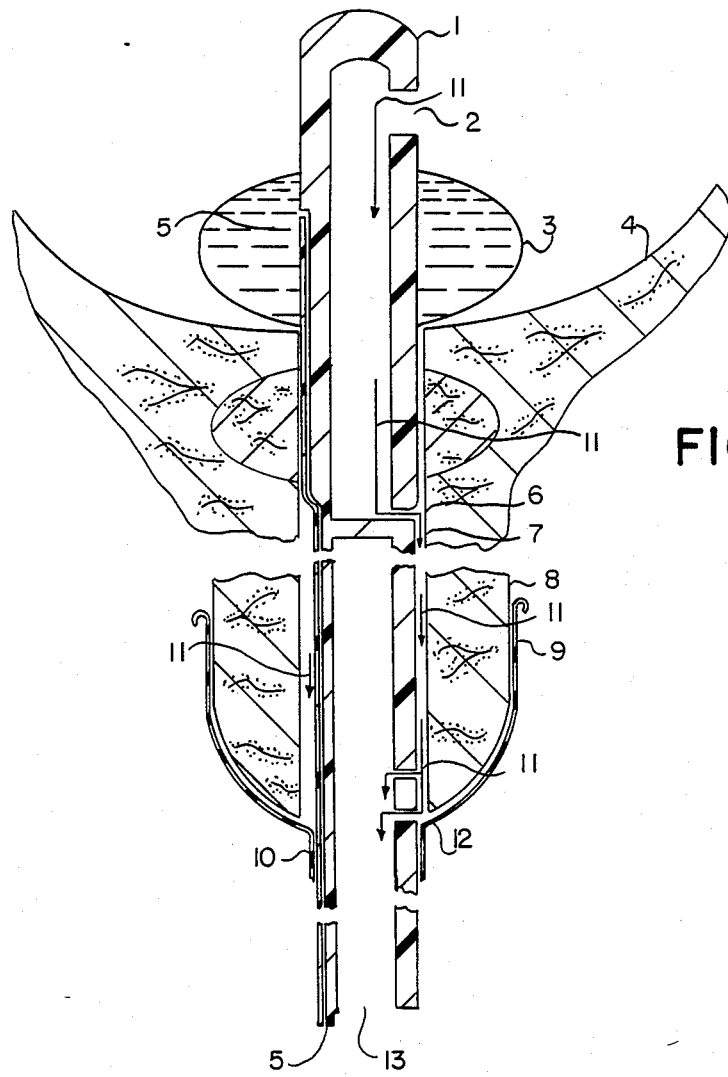

FIG. 2: A longitudinal section of the condom catheter in an embodiment provided with a balloon at the tip of the catheter.

Figure 3:
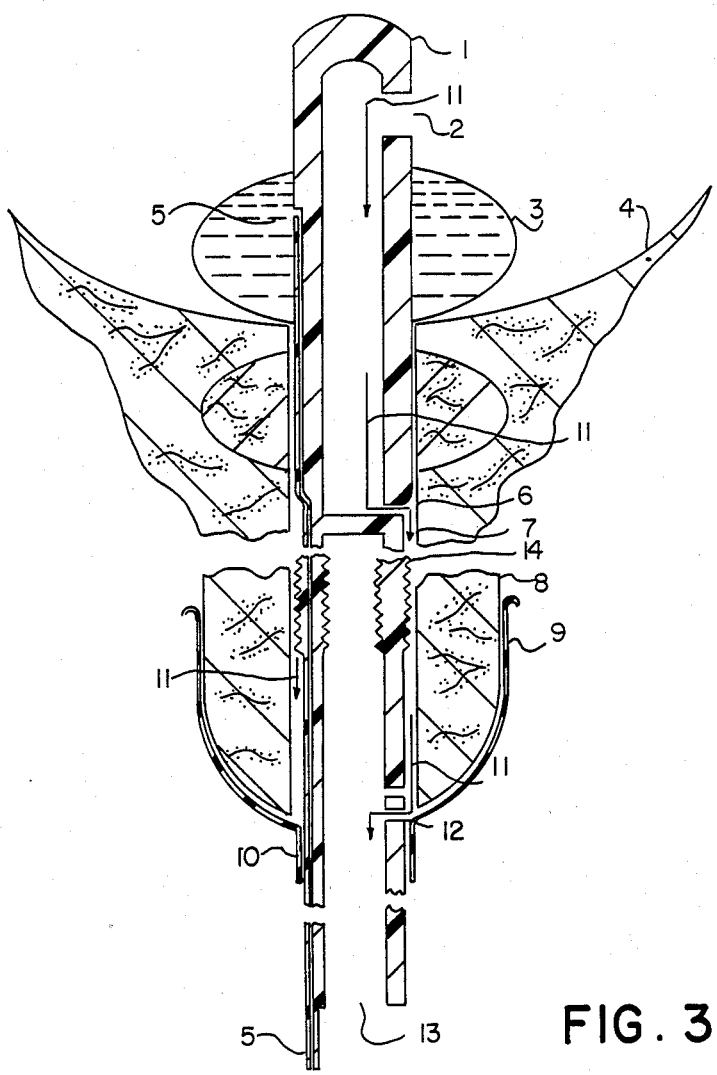

FIG. 3: A longitudinal section of the condom catheter in an embodiment of the invention equipped with an extensible middle section.

Figure 4:
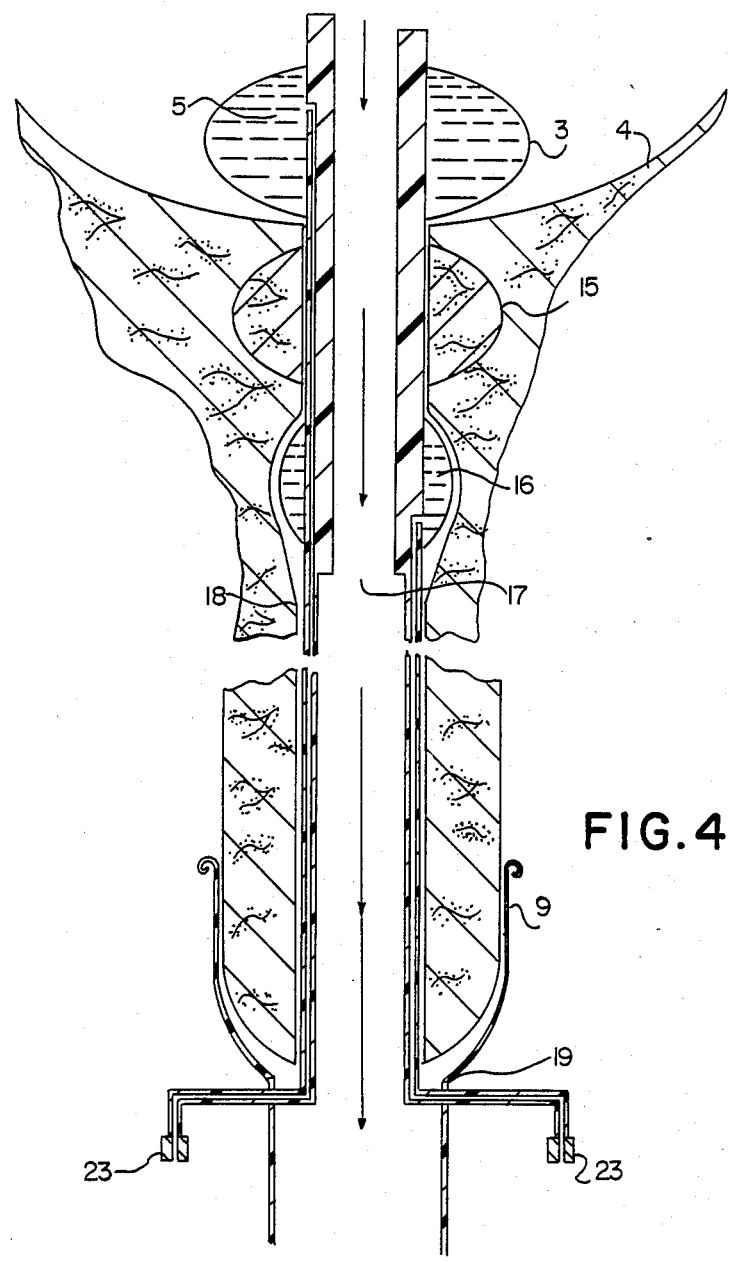

FIG. 4: A longitudinal section of the condom catheter in its embodiment as an inner urethral catheter.

Figure 5A:
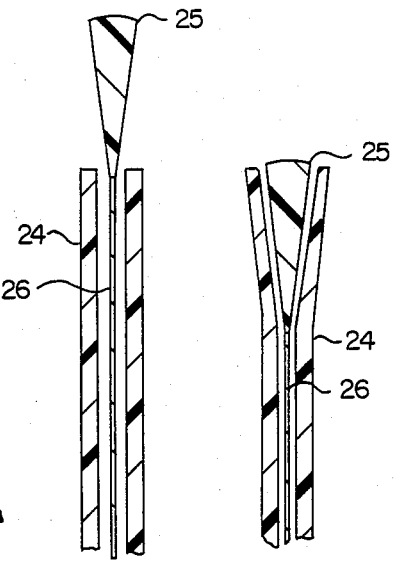

FIG. 5a: A longitudinal section of the guiding mandrin for the inner urethral catheter without tip expansion, and FIG. 5b: A longitudinal section of the guiding mandrin for the inner urethral catheter with tip expansion.

FIG. 1 shows with 1 the catheter tip reaching into the bladder, in the region of which at 2 the bladder urine enters into the catheter lumen 26 in the direction of the urinary stream 11. In the area of the sphincter of the bladder and the prostate gland 15 the urinary stream flows inside the catheter shaft 25 and passes at the point where the catheter shaft leaves the prostate sphincter through one or several openings 6 into the gap between catheter shaft wall and urethral wall. Toward the urethral orifice, the urethral lumen is interrupted by a stopper 27, so that the urinary stream is at this point positively directed to the outside. The urine now flows over long sections between catheter shaft and urethral wall in the direction of the urethral orifice. In the region of the urethral orifice the urine re-enters through one or several openings 12 into the catheter lumen 26 and flows through the catheter lumen toward that area where the urine collecting vessels are connected. Urine quantities which fail to re-enter into the catheter lumen through the orifices 6 are trapped in the condom-like sheath and forced to enter into the catheter lumen.

In the embodiment shown in FIG. 2 there is, in addition to the embodiment shown in FIG. 1, a balloon 3 provided in the region of the catheter tip 1, which can be inflated with a liquid medium or gas through the filling channel 5. Said balloon 3 holds the catheter tip in place inside the bladder.

The application possibilities of the embodiment shown in FIG. 2 are, however, restricted in the case of still occurring penis erections due to the change in length of the penis. This would result in a compression of the penis shaft. This disadvantage is overcome by the embodiment of the invention shown in FIG. 3. Here, the catheter shaft is configured in its middle section 14 in a fashion similar to the bellows of an accordion making it extensible upon the application of a light tension.

Figure 5B:
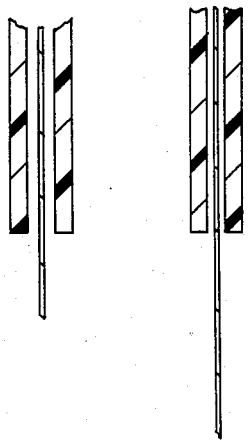

In the embodiment represented in FIG. 4 a catheter shaft proper exists only in the bladder sphincter/prostate region 15. In the remaining part of the urethra there are only the two thin tubes accomodating the filling channels for the two balloons. The catheter shaft is kept in its correct position between bladder and posterior region of the anterior urethra by the two balloons 3 and 6. As in all other embodiments shown, here as well the bladder urine will enter into the catheter lumen through the urine inlet opening 2. However, in this embodiment the catheter shaft 25 is wide open at 17, and the urine will flow directly into the posterior section of the anterior urethra, and inside the urethra further toward the urethral orifice, whereby the two narrow tubes for the filling channels are situated within said urinary stream. In the region of the urethral orifice the urine is again collected inside the condom-like penis sheath and drained by means of a tube. The tubes of the filling channels should suitably be guided to the outside at this point. The ends of said tubes are fitted with small filling nozzles 29 of the commercially available type. In view of the fact that a catheter designed in this fashion cannot be introduced due to lack of stability, a guiding mandrin as represented in FIGS. 5a and 5b will be required. It principally consists of a tube 24 made from an elastic material, which is simply cut open at one or several places in its tip region.

The diameter of said mandrin tube is matched to the lumen of the inner catheter. By pulling in the cone 23 which sits on a flexible push-pull bar 30, the tip can be expanded to increase its diameter and thus be clamped tight inside the lumen of the inner catheter. When the cone is pushed out, the diameter of the mandrin tip will decrease again.

Item Reference List

1 Catheter tip
2 Urine inlet opening
3 Catheter balloon in the bladder region
4 Bladder wall
5 Filling channel for the catheter balloon in the bladder region
6 Urine outlet opening in the region of the urethra
7 Inner wall of the urethra
8 Penis shaft
9 Condom-like sheath over the penis shaft
10 Collar of the condom-like sheath
11 Urinary stream
12 Urine inlet opening to the catheter lumen
13 Urine outlet from the catheter, transition to urine drainage
14 Accordion-like elastic catheter shaft section
15 Bladder sphincter - prostate region
16 Catheter balloon in the bulbous portion of the urethra
17 Clear lumen of the inner catheter in the direction of the urethral orifice
18 Filling channel for the catheter balloon in the bulbous portion of the urethra
19 Tube connection of the condom-like sheath
20 Catheter shaft
21 Catheter lumen
22 Catheter lumen stopper
23 Balloon filling nozzle
24 Mandrin shaft
25 Mandrin cone
26 Push-pull bar

I claim:

1. Indwelling urethral catheter arrangement for the prevention of ascending bacterial infection, comprising
a catheter shaft having an upper section with a diameter sufficiently large to substantially prevent passage of urine externally thereof, and a lower section at least a part of which is of reduced diameter, said catheter shaft having lateral outlet opening means near the upper end of said part, lateral inlet opening means at a lower point of said part and lumen stopper means intermediate said outlet and inlet opening means so that the urinary stream is deflected for relatively free flow over the distance defined by said opening means to the generally annular space between the urethral wall and the outside of said catheter shaft, and a condom-like sheath in the region of said lower end, said sheath at its bottom having an aperture surrounding the lower section of said catheter shaft in sealing relationship, and at its top being fittable over the penis,
so that, on the one hand, the bacteria are flushed downwardly by the urinary stream and, on the other hand, the entire urinary stream is conducted in a leakproof manner to the outside of said catheter arrangement.

2. Indwelling urethral catheter arrangement as claimed in claim 1,
wherein said catheter is provided with a positioning balloon in the region of the catheter tip, and with a filling tube for inflating said balloon.

3. Indwelling urethral catheter arrangement as claimed in claim 1,
wherein the catheter shaft in said part has an accordionlike configuration so as to permit the length of said shaft to automatically adjust itself to the length of the penis.

4. Indwelling urethral catheter arrangement for the prevention of ascending bacterial infection, comprising
a catheter shaft of limited length and having a diameter sufficiently large to substantially prevent passage of urine externally thereof, so as to permit the urinary stream of flow relatively freely underneath said shaft substantially over the entire area corresponding to the full cross-section of the shaft,
said shaft being provided with a first positioning balloon in the region of the catheter tip and with a second positioning balloon in the region of the lower end of the catheter shaft, and with filling tubes for the first and second balloons, respectively, and
a drainage tube separate from said catheter shaft at the lower end of said catheter arrangement, for permitting the urinary stream to exit from said catheter arrangement, and a condom-like sheath in the region of said lower end, said sheath at its bottom having an aperture adjoining said drainage tube in sealing relationship, and at its tip being fittable over the penis, so that on the one hand, the bacteria are flushed downwardly by the urinary stream and, on the other end, the entire urinary stream is conducted in a leakproof manner to the outside of said catheter arrangement.

5. Indwelling urethral catheter arrangement as claimed in claim 4, wherein said filling tubes are laterally guided through, and to the outside of said drainage tube.

* * * * *

UNITED STATES PATENT AND TRADEMARK OFFICE
CERTIFICATE OF CORRECTION

PATENT NO. : 4,878,901

DATED : Nov. 7, 1989

INVENTOR(S) : Hans-Ernst SACHSE

It is certified that error appears in the above-identified patent and that said Letters Patent is hereby corrected as shown below:

Col. 1, line 9  "ascent" should be -- ascend --

Claim 4, Col. 4, line 57  "of" should be -- to --

Signed and Sealed this

Eighteenth Day of September, 1990

Attest:

HARRY F. MANBECK, JR.

*Attesting Officer*  *Commissioner of Patents and Trademarks*